United States Patent [19]
Ramirez de Agudelo et al.

[11] Patent Number: 6,049,012
[45] Date of Patent: Apr. 11, 2000

[54] CATALYST AND PROCESS FOR THE PRODUCTION OF ALKYL TERT ALKYL ETHER FROM HYDROCARBON FEEDSTOCKS WITH HIGH LEVELS OF SULFUR

[75] Inventors: Magdalena Ramirez de Agudelo, Miranda; Trino J. Romero, Caracas; Emilia Mujica, San Antonio de Los Altos, all of Venezuela

[73] Assignee: Intevep, S.A., Caracas, Venezuela

[21] Appl. No.: 08/455,224

[22] Filed: May 31, 1995

Related U.S. Application Data

[62] Division of application No. 08/292,832, Aug. 19, 1994.
[51] Int. Cl.[7] .................................................. C07C 41/06
[52] U.S. Cl. ........................... 568/697; 568/694; 568/695
[58] Field of Search ..................................... 568/697, 695, 568/694

[56] References Cited

U.S. PATENT DOCUMENTS 5,382,706   1/1995   Gonzalez et al. ....................... 568/697

*Primary Examiner*—Paul J. Killos
*Assistant Examiner*—Dwayne C. Jones
*Attorney, Agent, or Firm*—Bachman & LaPointe, P.C.

[57] ABSTRACT

A catalyst for production of alkyl tert alkyl ether from sulfur contaminated feedstock includes an ion exchange resin; a palladium first metal phase supported on the resin; and a sulfur inhibiting second metal phase supported on the resin for inhibiting sulfur deactivation of the first metal phase, wherein the first metal phase is present at an atomic ratio to the second metal phase of between about 1:20 to about 1:0.1. A process for producing alkyl tert alkyl ethers includes the steps of providing a liquid olefinic hydrocarbon feedstock containing sulfur and having a total sulfur content of up to about 300 ppm; providing a catalyst as described above; mixing the feedstock with alcohol and hydrogen to obtain a reaction feedstock; and contacting the reaction feedstock with the catalyst under etherification conditions so as to produce alkyl tert alkyl ether.

8 Claims, No Drawings

CATALYST AND PROCESS FOR THE PRODUCTION OF ALKYL TERT ALKYL ETHER FROM HYDROCARBON FEEDSTOCKS WITH HIGH LEVELS OF SULFUR

This is a Division of application Ser. No. 08/292,832, filed Aug. 19, 1994.

BACKGROUND OF THE INVENTION

The invention relates to a catalyst and a process for producing alkyl tert alkyl ethers from sulfur contaminated feedstocks wherein the catalyst has enhanced resistance to sulfur deactivation.

Alkyl tert alkyl ethers such as MTBE, TAME, ETBE and the like are useful as fuel additives or extenders and as octane improving agents for unleaded gasolines.

Numerous processes and catalysts are known for production of alkyl tert alkyl ethers. Such processes typically involve reaction of a primary alcohol with an olefin having a double bond on a tertiary carbon atom. Ion exchange resins are particularly useful for such processes. Etherification and isomerization processes and catalyst resins for such processes are disclosed in U.S. Pat. Nos. 4,330,679, 4,695,556 and 5,008,466.

Light hydrocarbon streams such as $C_4$–$C_{10}$ streams from FCC processes and the like are potentially desirable feedstocks for etherification processes. However, FCC hydrocarbon streams and others have been found to rapidly deactivate the ion exchange resin catalyst thereby making the process inefficient and costly.

It is desirable to provide a catalyst and an etherification process using the catalyst wherein the catalyst is not rapidly deactivated.

It is therefore the primary object of the present invention to provide an ion exchange resin catalyst for use in preparing alkyl tert alkyl ethers wherein the resin is resistant to rapid deactivation.

It is a further object of the invention to provide a process utilizing the catalyst of the present invention to produce alkyl tert alkyl ethers.

Other objects and advantages will appear herein below.

SUMMARY OF THE INVENTION

The foregoing objects and advantages are readily attained by the present invention.

In accordance with the invention, a catalyst is provided which comprises an ion exchange resin; a palladium first metal phase supported on the resin; and a sulfur inhibiting second metal phase supported on the resin for inhibiting sulfur deactivation of the first metal phase, wherein the first metal phase is present at an atomic ratio to the second metal phase of between about 1:20 to about 1:0.1.

In further accordance with the invention, a process is provided for producing alkyl tert alkyl ethers which comprises the steps of providing a liquid olefinic hydrocarbon feedstock containing sulfur and having a total sulfur content of up to about 300 ppm; providing a catalyst comprising an ion exchange resin; a palladium first metal phase supported on the resin, and a sulfur inhibiting second metal phase supported on the resin for inhibiting sulfur deactivation of the resin and the first metal phase, wherein the first metal phase is present at an atomic ratio to the second metal phase of between about 1:20 to about 1:0.1; mixing the feedstock with alcohol and hydrogen to obtain a reaction feedstock; and contacting the reaction feedstock with the catalyst under etherification conditions so as to produce alkyl tert alkyl ether.

DETAILED DESCRIPTION

The invention is drawn to an ion exchange resin catalyst for use in the production of alkyl tert alkyl ethers such as methyl tert butyl ether (MTBE), tert amyl methyl ether (TAME), ethyl tert butyl ether (ETBE), and the like. In accordance with the invention, it has been found that sulfur in the feedstock to be treated is responsible for the rapid deactivation of the ion exchange resin and active metal contained thereon. In accordance with the invention, therefore, a catalyst is provided which possesses enhanced resistance to sulfur deactivation and is therefore desirable for use in treating sulfur containing feedstocks such as $C_4$–$C_{10}$ FCC or naphtha feedstock containing sulfur so as to provide alkyl tert alkyl ethers as desired.

In accordance with the invention, a suitable ion exchange resin is provided and supports a first active metal phase, preferably palladium (Pd), for enhancing the activity of the catalyst toward desired etherification, hydrogenation and isomerization reactions. A second active metal phase is also provided on the resin according to the invention which serves to reduce the effects of sulfur on the palladium and resin and thereby extend the useful life of the resin for treating sulfur contaminated feedstock.

Preferable ion exchange resins include macroporous polystyrene resin cross-linked with divinylbenzene and having a degree of crosslinking of between about 5% to about 65%, preferably between about 5% to about 35%. The resin in accordance with the invention has been found to be particularly useful in acid form.

In accordance with the invention, the resin is preferably doped or otherwise provided with the first metal phase and the second metal phase so as to provide a bimetallic ion exchange resin catalyst useful in accordance with the invention to produce MTBE, TAME, ETBE and the like.

As set forth above, the first metal phase is preferably palladium, which has been found according to the invention to enhance the activity of the resin and to provide a trifunctional catalyst which is active toward desired etherification, hydrogenation and double bond isomerization reactions. Palladium is preferably provided on the resin so as to be present in an amount by weight of the final catalyst of between about 0.01% to about 10.0%.

In further accordance with the invention, the second metal phase is provided so as to increase the number of active sites on the resin and to more strongly interact with sulfur than the palladium so that the palladium sites are not inhibited by sulfur. Because sulfur acts as a Lewis base or electron donor, the second metal preferably has a higher attraction for electrons, or electrophilicity, than does the palladium.

Thus, in accordance with the invention, the second metal is preferably a metal having a d5 or d10 electron configuration. According to the invention, d5 and d10 metals interact with sulfur more strongly than palladium and therefore interact with a substantial amount of the sulfur present in the feedstock, thereby preventing sulfur deactivation of the palladium. Further, because such interaction is believed to be by adsorption, the sulfur is attracted in a reversible fashion, thereby providing a resin which desirably may be reactivated after extensive use. Particularly suitable metals for the second metal include iron, ruthenium, nickel, zinc, manganese, silver, gold, copper and cobalt, most preferably copper, nickel, zinc, silver and iron. In accordance with the invention, the foregoing metals are useful as sulfur inhibitors on the resin and are further useful in any state of oxidation.

The resin is preferably doped or otherwise provided with the first and second metal so as to provide an atomic ratio of first metal to second metal of between about 1:20 to about 1:0.1, more preferably between about 1:10 to about 1:0.5.

Resins in accordance with the invention are useful in producing desired alkyl tert alkyl ethers despite the presence of sulfur in the feedstock. The second metal added as per the present invention serves to provide improved resistance to deactivation of sites responsible for desired etherification, selective diolefin hydrogenation and double bond isomerization reactions over resins without the second metal as illustrated in the examples presented below.

In accordance with the invention, resins doped with first and second metals as described are useful in treating feedstocks with sulfur contents of up to about 300 ppm, even when sulfur is present in the form of mercaptan, which has been found to be particularly harmful to the catalyst, in amounts up to about 200 ppm.

In accordance with the process of the present invention, alkyl tert alkyl ethers are provided as desired using the catalyst of the present invention with sulfur containing feedstocks without rapid deactivation of the catalyst.

According to the process of the present invention, a liquid olefinic feedstock is provided which may preferably be a $C_4$–$C_{10}$ light hydrocarbon or naphtha stream such as an FCC stream, coking process stream, cracking process stream and the like. The feedstock preferably contains about 2–40% iso-olefin and about 0.2–2.5% diolefin by weight of the feedstock.

The feedstock to be treated may suitably have a total sulfur content of up to about 300 ppm, and may contain sulfur in mercaptan form of up to about 200 ppm.

According to the invention, the feedstock is mixed with suitable amounts of alcohol and hydrogen to provide a reaction feedstock.

The alcohol reacts with olefins in the feedstock so as to provide desired etherification thereby yielding alkyl tert alkyl ether products. Alcohol is preferably added and mixed with the feedstock in amounts sufficient to provide a molar ratio of alcohol to tertiary olefin in the feedstock of between about 0.5 to about 3.0. Suitable alcohols include, for example, methanol, ethanol, propanol, isopropanol, butanol, isobutanol and the like and mixtures thereof.

Hydrogen reacts with the feedstock to help provide the desired hydrogenation and double bond isomerization reactions in accordance with the invention. Hydrogen is preferably mixed in amounts sufficient to provide a molar ratio of hydrogen to diolefins in the feedstock of between about 0.5 to about 4. 0. It should be noted that hydrogenation of diolefins is advantageous in preventing formation of gums which tend to foul the catalyst and adversely affect same.

The reaction feedstock is then contacted with the catalyst of the present invention under process conditions so as to provide the desired etherification, hydrogenation and isomerization reactions and to thereby produce alkyl tert alkyl ether and other desirable products. The process conditions preferably include a pressure of between about 10 to about 25 bars, a temperature of between about 40 to about 90° C., and a space velocity (LHSV) of between about 0.5 to about 5.0 $h^{-1}$.

In accordance with the invention, a trifunctional resin catalyst is provided which is active toward enhancing etherification, hydrogenation and double bond isomerization of a sulfur-containing feedstock with enhanced resistance of the resin to sulfur deactivation.

In accordance with the process of the invention, sulfur-containing feedstocks are treated so as to provide useful alkyl tert alkyl ethers and other desirable products.

The following examples illustrate the characteristics of the catalyst and process according to the invention.

EXAMPLE 1

This example compares the sulfur resistance of catalysts doped with palladium and a second metal in accordance with the invention to a catalyst doped only with palladium. Five catalysts were prepared using macroporous polystyrene resin crosslinked with divinylbenzene and doped with metal (s) as summarized in Table 1 below.

TABLE 1

| Catalyst | Pd content (g/l) | 2nd metal | 2nd metal content (g/l) |
|---|---|---|---|
| A | 1 | None | — |
| B | 1 | Ni | 1 |
| C | 1 | Cu | 1 |
| D | 1 | Ag | 1 |
| E | 1 | Fe | 1 |

A feedstock was provided having a composition as set forth below in Table 2.

TABLE 2

| $C_4$ | 6.27% (wt) |
|---|---|
| $C_5$ | 60.5% |
| Iso-$C_5$ | 18.23 |
| Diolefin | 1.48 |
| Methanol/Iso-$C_5$ | 1.58 |
| $C_6$ | 18.8 |

Each catalyst was tested first with a clean feedstock as identified in Table 2 above, and then with a feedstock containing 700 ppm n-butylmercaptan. The tests were carried out using 10 cc catalyst samples initially treated with methanol under a flow of 8 cc/h, and activated for 12 hours at 80° C., 300 psi of $H_2$ at 40 cc/min. The reaction mixture feedstock was fed to the reactor at a LHSV of 3 $h^{-1}$, at 70° C., 300 psi and 40 cc/min of $H_2$. Table 3 summarizes the results of this test. For each catalyst, the relative activity is given. Relative activity in this case is a ratio of the activity of the catalyst after 6 hours of treatment with the sulfur feedstock to the activity of the catalyst in treating the feedstock without sulfur.

TABLE 3

| Catalyst | Hydrogenation | Isomerization |
|---|---|---|
| A | 0.70 | 0.15 |
| B | 0.80 | 0.12 |
| C | 1.00 | 0.33 |
| D | 0.72 | 0.17 |
| E | 0.70 | 0.12 |

As illustrated, the catalyst according to the present invention, especially catalyst C, exhibited significantly improved resistance to sulfur deactivation as compared to catalyst A with only palladium, even under the extreme sulfur conditions of this example.

EXAMPLE 2

This example is to demonstrate the effect of larger amounts of the second metal in the catalyst. Three catalysts (B1, B2 and B3) were prepared similarly to Example 1 with different amounts of Ni as shown below in Table 4.

TABLE 4

| Catalyst | Pd ppm | Ni ppm | Surface Ni/Pd |
|---|---|---|---|
| B1 | 2200 | 2482 | 1.87 |
| B2 | 2300 | 5224 | 2.53 |
| B3 | 2120 | 21900 | 5.33 |

A reactor was loaded with 135cc of each catalyst of Table 4 and 67 cc of etherification resin. Each catalyst was tested with a feedstock having a composition as shown below in Table 5 at similar conditions to those set forth above and at a feedstock flow rate (methanol and naphtha) of 404 ml/h.

TABLE 5

| $C_4$ | 8.63% (wt) |
|---|---|
| $C_5$ | 75.6% |
| $C_6$ | 5.63% |
| I-$C_4$ | 0.85% |
| I-$C_5$ | 22.14% |
| Methanol | 7.7% |
| Total diene | 1.54% |
| Total sulfur | 49.5 ppm (no mercaptan) |

The activity of the catalysts for etherification, hydrogenation and isomerization was monitored every 24 hours during treatment of the feedstock. Table 6 sets forth the relative activity for each catalyst for treatment of the clean feedstock (Table 5) and with the same feedstock doped with 70 ppm n-butylmercaptan.

TABLE 6

| Catalyst | Hydrogenation | Etherification | Isomerization |
|---|---|---|---|
| B1 | 0.99 | 1.1 | 0.38 |
| B2 | 0.70 | 1.04 | 0.47 |
| B3 | 0.72 | 0.98 | 0.45 |

As shown, as the ratio of Ni to Pd increases, isomerization activity increases and hydrogenation activity decreases. Etherification is substantially constant. In accordance with the invention, activity of the catalyst may apparently be controlled by altering the ratio of second metal to palladium.

EXAMPLE 3

This example was carried out at a pilot plant to further illustrate the enhanced resistance of the catalyst of the present invention to deactivation by sulfur. Catalysts B–D as used in Example 1 were tested using a clean feedstock as described below in Table 7 and with the same feedstock doped with 100 ppm of n-butylmercaptan.

TABLE 7

| 3-M-1-butene | 0.69% (wt) |
|---|---|
| 2-M-2-butene | 11.94% |
| 2-M-1-butene | 5.41% |
| isoprene | 0.29% |
| 1-pentene | 2.75% |
| Other HC's | 64% |
| Diolefin | 1.01% |
| Methanol | 13.9% |

The reaction conditions were as follows: inlet reactor temperature 60° C., pressure 15 barg, LHSV 3 h$^{-1}$, H$_2$/dienes 2.

Table 8 sets forth the relative activity of the catalysts for activity measured after 24 hours and at the end of a four day run.

TABLE 8

| Catalyst | Hydrogenation | Isomerization |
|---|---|---|
| A | 0.90 | 0.84 |
| B | 0.98 | 0.86 |
| C | 0.95 | 0.96 |
| D | 0.84 | 1.0 |

As shown, catalysts B and C exhibited improved resistance to deactivation of both hydrogenation and isomerization activity as compared to catalyst A, while catalyst D illustrated further enhanced resistance to deactivation of isomerization activity.

In light of the above examples, it is clear that a catalyst has been provided in accordance with the invention which advantageously exhibits enhanced resistance to deactivation when used with sulfur containing feedstock. Further, a process is disclosed in accordance with the invention whereby the subject catalyst is used to produce desirable alkyl tert alkyl ether products from sulfur containing feedstock without rapid catalyst deactivation.

This invention may be embodied in other forms or carried out in other ways without departing from the spirit or essential characteristics thereof. The present embodiments are therefore to be considered as in all respects to be illustrative and not restrictive, the scope of the invention being indicated by the appended claims, and all changes which come within the meaning and range of equivalency are intended to be embraced therein.

What is claimed is:

1. A process for production of alkyl tert alkyl ether, comprising the steps of:

providing a liquid olefinic hydrocarbon feedstock containing sulfur and having a total sulfur content of up to about 300 ppm;

providing a catalyst comprising an ion exchange resin, a palladium first metal phase supported on the resin, and a sulfur inhibiting second metal phase supported on the resin for inhibiting sulfur deactivation of the first metal phase wherein the first metal phase is present at an atomic ratio to the second metal phase of between about 1:20 to about 1:0.1 and the second metal phase has a higher degree of electrophilicity than the palladium;

mixing the feedstock with alcohol and hydrogen to obtain a reaction feedstock; and contacting the reaction feedstock with the catalyst under etherification conditions so as to produce alkyl tert alkyl ether.

2. A process according to claim 1, wherein the catalyst is a trifunctional catalyst and wherein the contacting step includes etherification, hydrogenation and double bond isomerization reactions.

3. A process according to claim 1, wherein the mixing step includes mixing alcohol sufficient to provide a molar ratio of alcohol to tertiary olefin of between about 0.5 to about 3.0 and mixing hydrogen sufficient to provide a molar ratio of hydrogen to diolefin of between about 0.5 to about 4.0.

4. A process according to claim 1, wherein the feedstock is selected from the group consisting of $C_4$–$C_{10}$ FCC streams, $C_4$–$C_{10}$ coking process streams, and $C_4$–$C_{10}$ cracking process streams.

5. A process according to claim 1, wherein the feedstock contains less than or equal to about 200 ppm of sulfur in mercaptan form.

6. A process according to claim 1, wherein the etherification conditions include a pressure of between about 10 to about 25 bars, a temperature of between about 40 to about 90° C., and a space velocity (LHSV) of between about 0.5 to about 5.0 h$^{-1}$.

7. A process according to claim 1, wherein the alcohol is selected from the group consisting of methanol, ethanol, propanol, isopropanol, butanol, isobutanol, and mixtures thereof.

8. A process according to claim 1, wherein the second metal phase is selected from the group consisting of metals having a d5 electron configuration, metals having a d10 electron configuration, and mixtures thereof.

* * * * *